United States Patent
Sang et al.

(10) Patent No.: US 7,087,621 B2
(45) Date of Patent: Aug. 8, 2006

(54) BENZO- AND AZABENZODITHIAZOLE COMPOUNDS

(75) Inventors: Xiaopeng Sang, Glastonbury, CT (US); Xuhua Karen Du, Cheshire, CT (US); John F. Kadow, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/933,094

(22) Filed: Sep. 1, 2004

(65) Prior Publication Data

US 2005/0101646 A1    May 12, 2005

Related U.S. Application Data

(60) Provisional application No. 60/500,621, filed on Sep. 5, 2003.

(51) Int. Cl.
- *A61K 31/437*   (2006.01)
- *A61K 31/428*   (2006.01)
- *C07D 513/04*   (2006.01)
- *C07D 285/01*   (2006.01)

(52) U.S. Cl. ............... 514/301; 514/360; 548/123; 546/114

(58) Field of Classification Search ............ 548/123; 546/114
See application file for complete search history.

(56) References Cited

OTHER PUBLICATIONS

Wagner et al., Ber. 1963, 96, 1177-1186 (Cas Abstract Attached).*
Rabai et al. Journal of Molecular Structure 1996, 382(1), 13-21 (Cas Abstract Attached).*

* cited by examiner

*Primary Examiner*—Joseph K. McKane
*Assistant Examiner*—Jason M. Nolan
(74) *Attorney, Agent, or Firm*—Elliott Korsen

(57) ABSTRACT

The present invention provides compounds of formula I

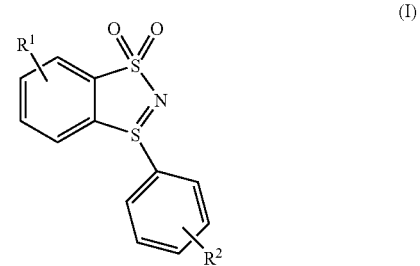

(I)

or a pharmaceutically acceptable salt, solvate, prodrug or isomer thereof and compounds of the formula

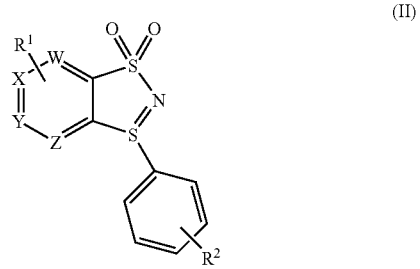

(II)

or a pharmaceutically acceptable salt, solvate, prodrug or isomer thereof.

The compounds of the invention inhibit tyrosine kinase activity of growth factor receptors such as HER1, HER2 and HER4 thereby making them useful as antiproliferative agents. The compounds are also useful for the treatment of other diseases associated with signal transduction pathways operating through growth factor receptors.

8 Claims, No Drawings

BENZO- AND AZABENZODITHIAZOLE COMPOUNDS

This application claims priority from U.S. Application Ser. No. 60/500,621 filed on Sep. 5, 2003 under 35 U.S.C. 119(e). The entire teachings of the referenced application are incorporated herein by reference.

FIELD OF THE INVENTION

This invention relates to compounds that inhibit the tyrosine kinase activity of growth factor receptors such as HER1, HER2 and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3 and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomyosarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

SUMMARY OF THE INVENTION

The compounds of the invention inhibit the tyrosine kinase activity of growth factor receptors such as HER1, HER2 and HER4 and as such, can be used to treat diseases that are associated with signal transduction pathways operating through growth factor receptors. For example, the compounds of the instant invention can be used as antiproliferatives and anticancer agents. More specifically, the invention comprises a compound of formula I

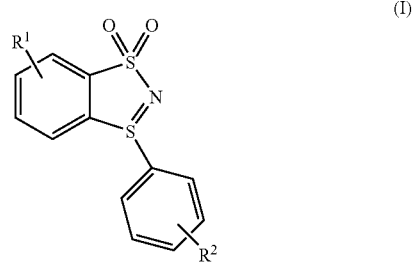

(I)

wherein the symbols have the following meanings and are, for each occurrence, independently selected:

$R^1$ is one or more hydrogen, alkyl, aryl, halogen, $CF_3$, $NH_2$, $NO_2$, cyano, COOH, COOalkyl, $CONR_3R_4$, NHCOalkyl, NHCOaryl, $NHSO_2$alkyl, $NHSO_2$aryl or NHCOalkoxyaryl, said aryl groups optionally substituted with one or more groups selected from alkyl, $NO_2$ or halogen;

$R^2$ is one or more alkyl, alkoxy, halogen, hydroxy, aryloxy, NHCOalkyl, $CONR_3R_4$, $CF_3$ or $NO_2$;

$R^3$ and $R^4$ are independently hydrogen, alkyl, substituted alkyl, halogen, alkoxy, substituted alkoxy, aryl or substituted aryl;

or a pharmaceutically acceptable salt, solvate, prodrug or isomer thereof.

There are also disclosed compounds of the formula

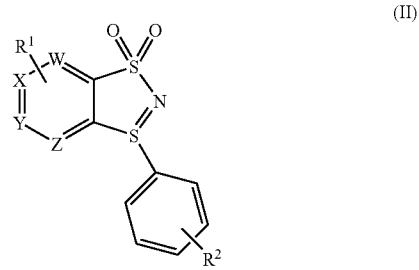

(II)

wherein the symbols have the following meanings and are, for each occurrence, independently selected:

$R^1$ is one or more hydrogen, alkyl, aryl, halogen, $CF_3$, $NR_3R_4$, $NO_2$, cyano, COOH, COOalkyl, $CONR_3R_4$, NHCOalkyl, NHCOaryl, $NHSO_2$alkyl or $NHSO_2$aryl, said aryl groups optionally substituted with one or more groups selected from alkyl, $NO_2$ or halogen;

$R^2$ is one or more alkyl, alkoxy, halogen, aryloxy, NHCOalkyl, $CONR_3R_4$, $CF_3$ or $NO_2$;

$R^3$ and $R^4$ are independently hydrogen, alkyl, substituted alkyl, halogen, alkoxy, substituted alkoxy, aryl or substituted aryl;

and one or more of W, X, Y and Z is N;

or a pharmaceutically acceptable salt, solvate, prodrug or isomer thereof.

Also provided for is a method for treating proliferative diseases, comprising administering to a mammalian species in need thereof, a therapeutically effective amount of a compound of formula I.

DETAILED DESCRIPTION OF THE INVENTION

The present invention provides for compounds of formula I, pharmaceutical compositions employing such compounds and for methods of using such compounds.

In accordance with the present invention, compounds of formula I

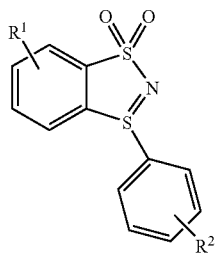

(I)

wherein the symbols have the following meanings and are, for each occurrence, independently selected:

$R^1$ is one or more hydrogen, alkyl, aryl, halogen, $CF_3$, $NH_2$, $NO_2$, cyano, COOH, COOalkyl, $CONR_3R_4$, NHCOalkyl, NHCOaryl, $NHSO_2$alkyl, $NHSO_2$aryl or NHCOalkoxyaryl, said aryl groups optionally substituted with one or more groups selected from alkyl, $NO_2$ or halogen;

$R^2$ is one or more alkyl, alkoxy, halogen, hydroxy, aryloxy, NHCOalkyl, $CONR_3R_4$, $CF_3$ or $NO_2$;

$R^3$ and $R^4$ are independently hydrogen, alkyl, substituted alkyl, halogen, alkoxy, substituted alkoxy, aryl or substituted aryl;

or a pharmaceutically acceptable salt, solvate, prodrug or isomer thereof.

There are also disclosed compounds of the formula

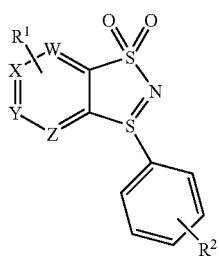

(II)

wherein the symbols have the following meanings and are, for each occurrence, independently selected:

$R^1$ is one or more hydrogen, alkyl, aryl, halogen, $CF_3$, $NR_3R_4$, $NO_2$, cyano, COOH, COOalkyl, $CONR_3R_4$, NHCOalkyl, NHCOaryl, $NHSO_2$alkyl or $NHSO_2$aryl, said aryl groups optionally substituted with one or more groups selected from alkyl, $NO_2$ or halogen;

$R^2$ is one or more alkyl, alkoxy, halogen, aryloxy, NHCOalkyl, $CONR_3R_4$, $CF_3$ or $NO_2$;

$R^3$ and $R^4$ are independently hydrogen, alkyl, substituted alkyl, halogen, alkoxy, substituted alkoxy, aryl, aryl or substituted aryl;

and one or more of W, X, Y and Z is N;

that inhibit the tyrosine kinase activity of growth factor receptors such as HER2.

Preferred compounds of formula I of the invention are those wherein $R^1$ is hydrogen, halogen, $CF_3$, $NH_2$, $NO_2$, COOH, COOalkyl, $CONR_3R_4$, NHCOalkyl, NHCOaryl, $NHSO_2$alkyl, $NHSO_2$aryl or NHCOalkoxyaryl, said aryl groups optionally substituted with one or more groups selected from alkyl, $NO_2$ or halogen;

$R^2$ is one or more alkyl, alkoxy, halogen, hydroxy, aryloxy, NHCOalkyl, $CONR_3R_4$, $CF_3$ or $NO_2$;

$R^3$ and $R^4$ are independently hydrogen or, alkyl;

or a pharmaceutically acceptable salt, solvate, prodrug or isomer thereof.

Preferred compounds of formula II of the invention are those wherein $R^1$ is hydrogen, $NR_3R_4$, $NO_2$, $CONR_3R_4$, NHCOalkyl or NHCOaryl;

$R^2$ is one or more alkyl, alkoxy, halogen, aryloxy, $CF_3$ or $NO_2$;

$R^3$ and $R^4$ are independently hydrogen or, alkyl;

X is N and W, Y and Z are —CH—;

or a pharmaceutically acceptable salt, solvate, prodrug or isomer thereof.

The following are definitions of terms that may be used in the present specification. The initial definition provided for a group or term herein applies to that group or term throughout the present specification individually or as part of another group, unless otherwise indicated. The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclo, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclo. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aryloxy" refers to aryl radicals attached through an oxygen atom to other radicals.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol al kylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl) or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocyclos, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention includes all the possible stereoisomers and their mixtures. Paricularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of formula I and II may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309–396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, *Advanced Drug Delivery Reviews*, 8, 1–38 (1992);

It should further be understood that solvates (e.g., hydrates) of the compounds of formula I are also with the scope of the present invention. Methods of solvation are generally known in the art.

Use and Utility

The present invention is based on the discovery that the compounds of the invention are inhibitors of protein kinases. More specifically, compounds of the invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of a compound of the formula I or formula II, or a pharmaceutically acceptable salt thereof in the manufacture of a medicament for use in the production of an antiproliferative effect in a mammalian species such as a human being.

According to a further feature of the invention there is provided a method for producing an antiproliferative effect in a mammalian species, such as a human being, in need of such treatment which comprises administering to said animal an effective amount of a compound of formula I or formula II or a pharmaceutically acceptable salt thereof as defined herein before.

By virtue of their ability to inhibit HER1, HER2 and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor effficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agens such as Taxol®, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as anti-angiogenic agents. See the following documents and references cited therein: Schlessinger J., "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I or II may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example megestrol acetate), aromatase inhibitors (for example anastrozole, letrozole, borazole, exemestane), antihormones, antiprogestogens, antiandrogens (for example flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotepa; antimitotic agents (for example vinca alkaloids like vincristine and taxoids like Taxol® (paclitaxel), Taxotere® (docetaxel) and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols); biological response modifiers and proteasome inhibitors such as Velcade® (bortezomib).

As stated above, the formula I and II compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I or II are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I or II may also be useful in the treatment of diseases other than cancer that may be associated with signal transduction pathways operating through growth factor receptors such as HER1 (EGF receptor), HER2, or HER4.

The compounds of this invention may be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders, suspensions and the like. The compounds may be administered in a dosage range of about 0.05 to 300 mg/kg/day, preferably less than 200 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 μM ATP, and 4 μCi/ml [γ-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2 and HER4 kinases with $IC_{50}$ values between 0.001 and 25 μM. Preferred compounds have $IC_{50}$ values between 0.001–5.0 μM. More preferred compounds have $IC_{50}$ values between 0.001–1.0 μM. Most preferred compounds have $IC_{50}$ values between 0.001–0.1 μM.

A HERG potassium channel assay may be used to screen compounds for HERG activity (see Caballero R, et al., *Direct Effects of Candesartan and Eprosartan on Human Cloned Potassium Channels Involved in Cardiac Repolarization*, Molecular Pharmacology, Vol. 59, No. 4, pp. 825–36, 2001). Accordingly, preferred compounds have lower HERG assay activity.

Methods of Preparation

Certain compounds of formula I and II may generally be prepared according to the following schemes and the knowledge of one skilled in the art.

Scheme 1

Scheme 1 is a general procedure of the synthesis of some of the sulfilimine compounds of Formula I.

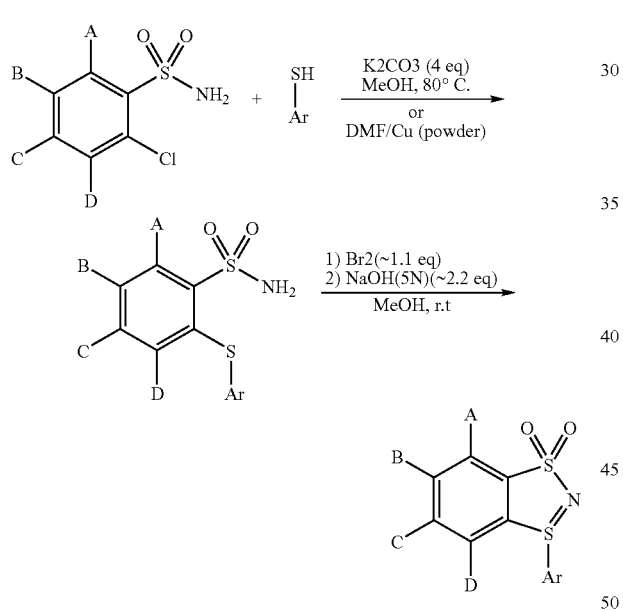

Scheme 2

Scheme 2 is an alternate synthesis of the compounds of Formula I.

MMPP is magnesium monoperoxypthalate hexahydrate.

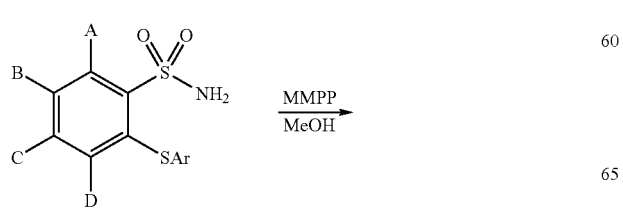

Scheme 3

Scheme 3 is a general procedure for the preparation of certain noncommercially available sulfonamides.

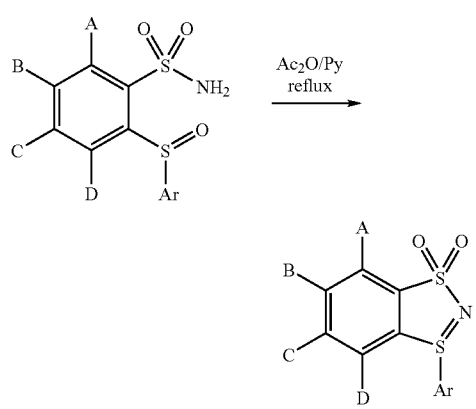

Scheme 4

Scheme 4 is a general procedure of the synthesis of some of the sulfilimine compounds of Formula II.

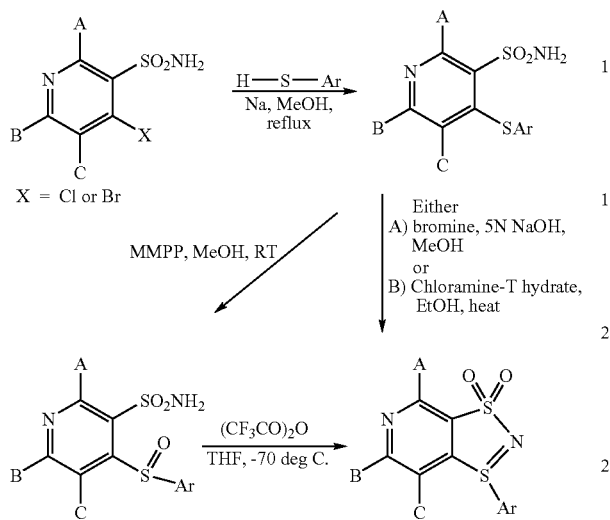

X = Cl or Br

Scheme 5

Scheme 5 is an alternate procedure for the synthesis of some of the sulfilimine compounds of Formula II.

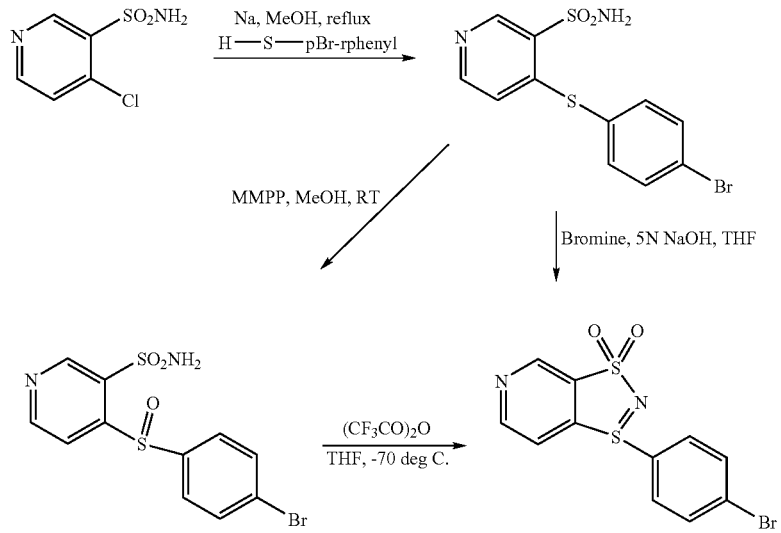

In addition, other compounds of formula I may be prepared using procedures generally known to those skilled in the art.

The invention will now be further described by the following working examples, which are preferred embodiments of the invention. These examples are illustrative rather than limiting, and it is to be understood that there may be other embodiments that fall within the spirit and scope of the invention as defined by the claims appended hereto.

EXAMPLE 1

Example 1 illustrates the preparation of a compound of the invention via a sulfide formation.

4-(4-Bromo-phenylsulfanyl)-pyridine-3-sulfonic acid amide

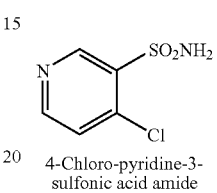

4-Chloro-pyridine-3-sulfonic acid amide

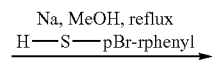

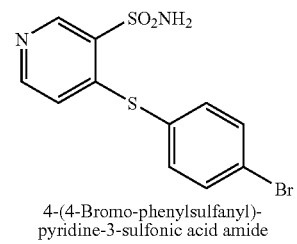

4-(4-Bromo-phenylsulfanyl)-pyridine-3-sulfonic acid amide 57.3 mg of solid sodium was added to 10.4 ml of methanol stirring at rt. After 15 min, 471 mg of 4-bromo benzene thiol was added and the reaction stirred for ~10 min. 4-chloro-pyridine-3-sulfonic acid (0.4 g) was added and the reaction refluxed for 4h. Water was slowly poured into the stirring reaction to precipitate the crude product which was collected by suction filtration and dried in vacuo to provide the desired product (0.70 g) as a white solid.

EXAMPLE 2

Example 2 illustrates the preparation of a compound of the invention via a cyclization from a sulfide.

1-(4-Bromo-phenyl)-1λ4,3-dithis-2,5-diaza-indene 3,3-dioxide

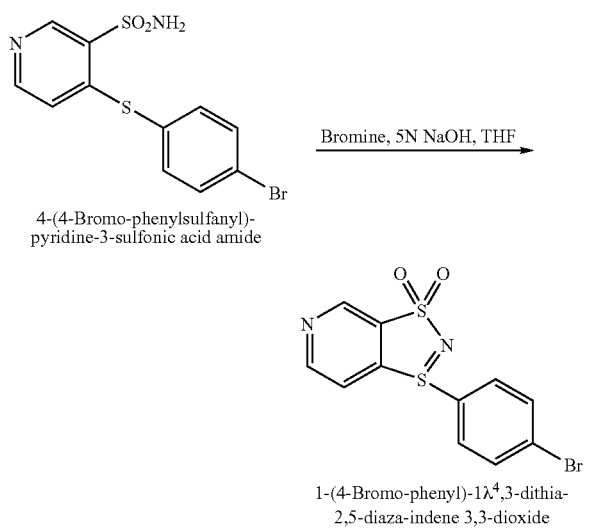

0.204 g (0.59 mmol) of 4-(4-bromo-phenylsulfanyl)-pyridine-3-sulfonic acid amide was dissolved in 6 mL of methanol. 57.5 μL of bromine (0.594 mmol) was added and the reaction stirred for 0.5h at RT. 0.24 mL of 5N NaOH was added. Stir approximately 1 h and dilute with ~50 mL EtOAC. Wash with water, sat aq. NaCl, dry over sodium sulfate. Purify via flash chromatography over SiO2 using a gradient of 40–90% EtOAc in hexane as eluent to provide 36 mg (28% yield) of the desired product and 75 mg of recovered starting material.

EXAMPLE 3

Example 3 illustrates the preparation of a compound of the invention via an oxidation of the sulfide to the sulfoxide.

4-(4-Bromo-benxenesulfinyl)-pyridine-3-sulfonic acid amide

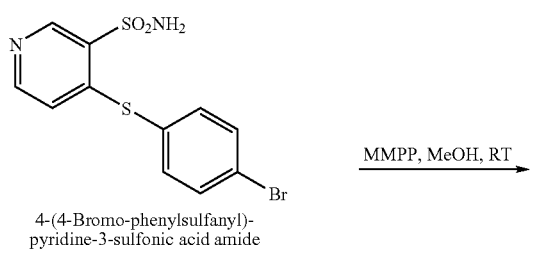

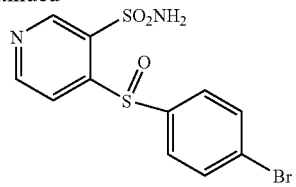

4-(4-Bromo-benzenesulfinyl)-pyridine-3-sulfonic acid amide

MMPP = Magnesium monoperoxypthalate hexahydrate 4-(4-Bromo-phenylsulfanyl)-pyridine-3-sulfonic acid amide 3.40 g, 0.985 mmol was suspended in 68 mL of MeOH. MMPP 3.42 g, 0.7 eq was added and the suspension quickly changed to a solution. The reaction was stirred for 1 h, diluted with approximately 150 mL EtOAc. The organic extracts were washed with ~50 mL water and the water layer extracted with ~100 mL EtOAc. Combined ethylacetate extracts were washed with sat. aq NaCl, dried over sodium sulfate and concentrated in vacuo. Trituration with MeOH, concentration in vacuo and trituration, concentration, and trituration provided three crops of white solid, which were combined to give 2.45 g of white solid (69% yield) of the desired compound 4-(4-Bromo-benzenesulfinyl)-pyridine-3-sulfonic acid amide.

EXAMPLE 4

Example 4 illustrates the preparation of a compound of the invention via a cyclization from the sulfoxide.

1-(4-Bromo-phenyl)-1l4,3-dithia-2,5-diaxa-indene 3,3-dioxide

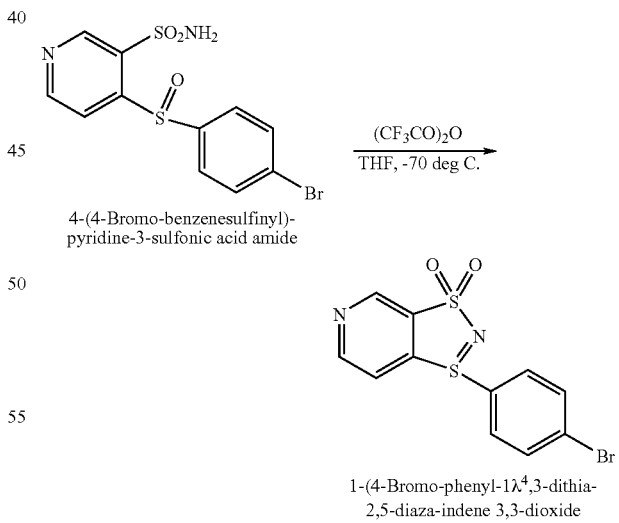

1.284 g of 4-(4-Bromo-benzenesulfinyl)-pyridine-3-sulfonic acid amide was dissolved in 33.8 mL of THF and cooled to −20° C. 1.91 mL (2 equivalents) of trifluoroacetic acid anhydride was added. After 15 minutes an additional 1.91 mL (2 eqs) of TFAA was added. The reaction was stirred for 3h, cooled to −30° C. and 33.8 mL of MeOH was added. Concentration on a rotary evaporator and trituration with methanol provided, after suction filtration and drying in vacuo, 0.7308 g of the desired product as a white solid.

EXAMPLE 5
Example 5 illustrates the preparation of a specific compound of the invention of formula I.
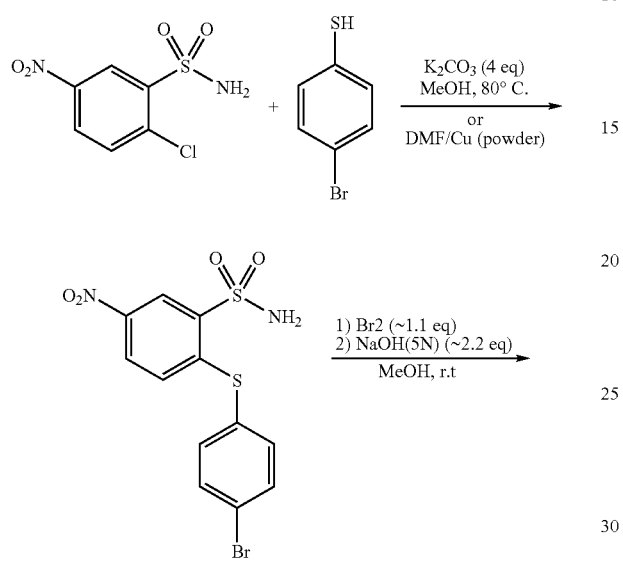
EXAMPLE 6
Example 6 illustrates an alternate preparation of a specific compound of the invention of formula I.
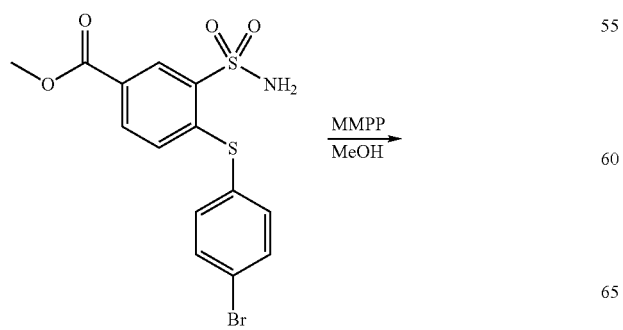
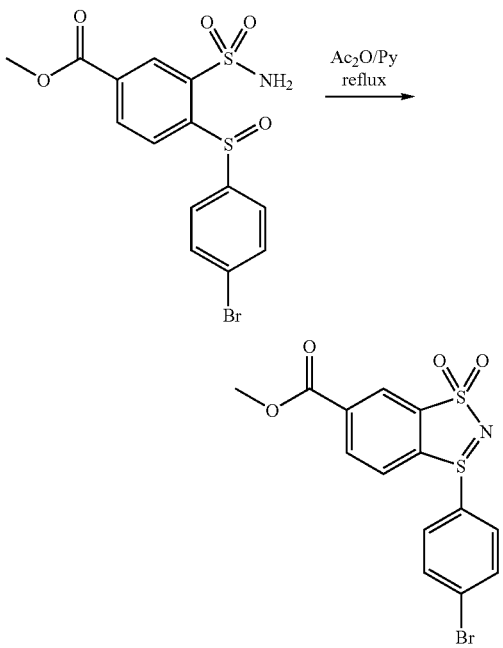
EXAMPLE 7
Example 7 illustrates the preparation of another specific compound of the invention of formula I.
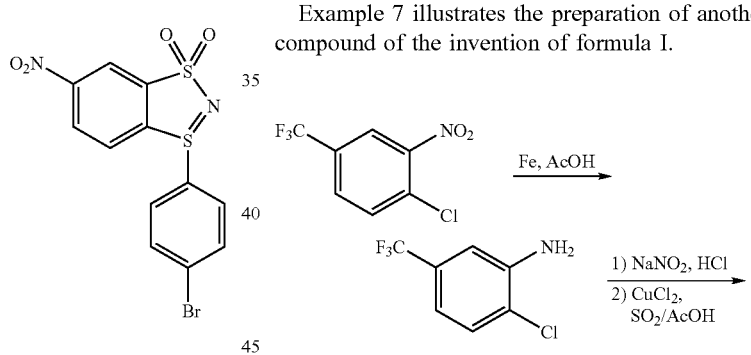
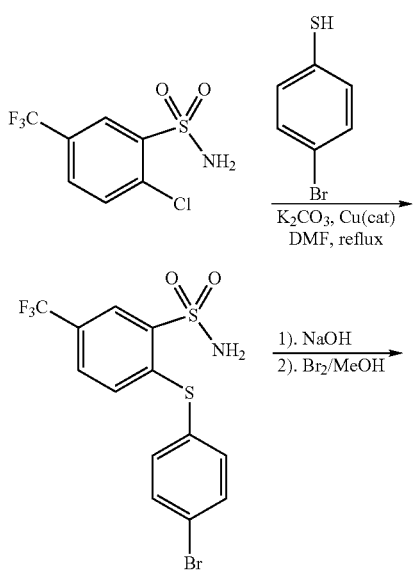

-continued

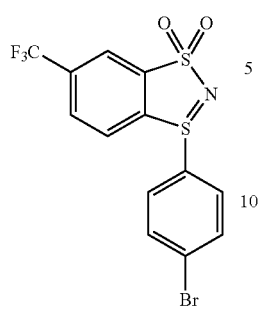

Compounds of formula I of the invention, prepared by the above schemes, include those wherein $R^1$ and $R^2$ are as defined in the following table:

| $R^1$ | $R^2$ |
|---|---|
| 5-NO$_2$ | p-Br |
| 4-NO$_2$ | p-Br |
| NO$_2$ | p-NO$_2$ |
| NO$_2$ | p-OCH$_3$ |
| NO$_2$ | H |
| NO$_2$ | p-CH$_3$ |
| NO$_2$ | o-OCH$_3$ |
| NH$_2$ | p-Br |
| NH$_2$ | p-NO$_2$ |
| NHCO(CH$_2$)$_6$CH$_3$ | p-Br |
| NHCO-Phenyl | p-Br |
| NHSO$_2$-Phenyl substituted with CH$_3$ | p-Br |
| NHCOCH$_2$O-Phenyl | p-Br |
| NHSO$_2$CH$_3$ | p-Br |
| NHCO-Phenyl substitued with NO$_2$ | p-Br |
| NO$_2$ | o-Br |
| NO$_2$ | o-CH(CH$_3$)$_2$ |
| NO$_2$ | o-CH$_2$OH |
| NO$_2$ | o-O-Phenyl |
| NO$_2$ | p-NHCOCH$_3$ |
| NO$_2$ | o-CONHCH$_3$ |
| NO$_2$ | m-Br |
| NO$_2$ | m-OCH$_3$ |
| NO$_2$ | m-CH$_3$ |
| NO$_2$ | 2,5 di-CH$_3$ |
| NO$_2$ | 2-Cl, 5-CH$_3$ |
| NO$_2$ | 3-CH$_3$, 4-Br, 5-CH$_3$ |
| NO$_2$ | 3,5 di-CF$_3$ |
| COOH | p-Br |
| COOCH$_3$ | p-Br |
| CONH$_2$ | p-Br |
| CF$_3$ | p-Br |
| F | p-Br |
| NO$_2$ | |
| NO$_2$ | p-F |
| NO$_2$ | |
| F | p-Br |

Compounds of formula II of the invention, prepared by the above schemes, include those wherein $R^1$ and $R^2$ are as defined in the following table:

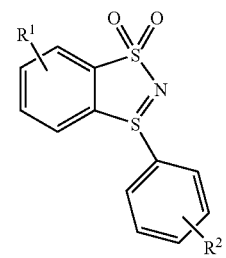

| $R^1$ | $R^2$ |
|---|---|
| H | p-Br |
| H | |
| H | p-CH$_3$ |
| H | |
| H | p-F |
| H | p-OH |
| H | m-OCH$_3$ |
| H | 3,5 di-CH$_3$ |
| H | p-OCH$_3$ |
| H | |
| H | m-Br |
| NH$_2$ | p-Br |
| H | p-Cl |
| H | p-CH(CH$_3$)$_2$ |
| NHCOCH$_3$ | p-Br |
| H | p-Br |
| H | p-Br |
| H | p-OCH$_2$-Phenyl substituted with Br |
| N(CH$_3$)$_2$ | p-Br |
| NHCO(CH$_2$)$_2$CH$_3$ | p-Br |
| | p-Br |
| | p-Br |
| NHCO-Phenyl | p-Br |

We claim:

1. A compound of formula I (I)

wherein the symbols have the following meanings and are, for each occurrence, independently selected:

$R^1$ is one or more hydrogen, alkyl, aryl, halogen, CF$_3$, NH$_2$, NO$_2$, cyano, COOH, COOalkyl, CONR$_3$R$_4$, NHCOalkyl, NHCOaryl, NHSO$_2$alkyl, NHSO$_2$aryl or NHCOalkoxyaryl, said aryl groups optionally substituted with one or more groups selected from alkyl, NO$_2$ or halogen;

$R^2$ is one or more alkoxy, hydroxy, aryloxy, NHCOalkyl, CONR$_3$R$_4$, CF$_3$ or NO$_2$;

$R^3$ and $R^4$ are independently hydrogen, alkyl, substituted alkyl, halogen, alkoxy, substituted alkoxy, aryl or substituted aryl;
or a pharmaceutically acceptable salt, solvate, prodrug or steroisomer thereof.

2. A compound of formula II

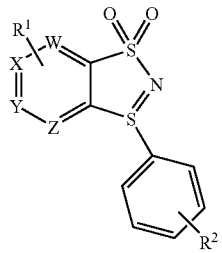

wherein the symbols have the following meanings and are, for each occurrence, independently selected:

$R^1$ is one or more hydrogen, alkyl, aryl, halogen, $CF_3$, $NR_3R_4$, $NO_2$, cyano, COOH, COOalkyl, $CONR_3R_4$, NHCOalkyl, NHCOaryl, $NHSO_2$alkyl or $NHSO_2$aryl, said aryl groups optionally substituted with one or more groups selected from alkyl, $NO_2$ or halogen;

$R^2$ is one or more alkyl, alkoxy, halogen, aryloxy, NHCOalkyl, $CONR_3R_4$, $CF_3$ or $NO_2$;

$R^3$ and $R^4$ are independently hydrogen, alkyl, substituted alkyl, halogen, alkoxy, substituted alkoxy, aryl or substituted aryl;

and one or more of W, X, Y and Z is N;

or a pharmaceutically acceptable salt, solvate, prodrug or steroisomer thereof.

3. The compound according to claim 1 wherein
$R^1$ is one or more hydrogen, halogen, $CF_3$, $NH_2$, $NO_2$, COOH, COOalkyl, $CONR_3R_4$, NHCOalkyl, NHCOaryl, $NHSO_2$alkyl, $NHSO_2$aryl or NHCOalkoxyaryl, said aryl groups optionally substituted with one or more groups selected from alkyl, $NO_2$ or halogen;
$R^2$ is one or more alkoxy, hydroxy, aryloxy, NHCOalkyl, $CONR_3R_4$, $CF_3$ or $NO_2$;
$R^3$ and $R^4$ are independently hydrogen or, alkyl;
or a pharmaceutically acceptable salt, solvate, prodrug or steroisomer thereof.

4. The compound according to claim 2 wherein
$R^1$ is one or more hydrogen, $NR_3R_4$, $NO_2$, $CONR_3R_4$, NHCOalkyl or NHCOaryl;
$R^2$ is one or more alkyl, alkoxy, halogen or aryloxy, $CF_3$ or $NO_2$;
$R^3$ and $R^4$ are independently hydrogen or, alkyl;

X is N and W,Y and Z are —CH—;
or a pharmaceutically acceptable salt, solvate, prodrug or steroisomer thereof.

5. A pharmaceutical composition comprising at least one compound of claim 1 and a pharmaceutically acceptable carrier.

6. A pharmaceutical composition comprising at least one compound of claim 1 in combination with a pharmaceutically acceptable carrier and at least one other anti-cancer or cytotoxic agent which is selected from the group consisting of tamoxifen, toremifen, raloxifene, droloxifene, iodoxifene, megestrol acetate, anastrozole, letrozole, borazole, exemestane, flutamide, nilutamide, bicalutamide, cyproterone acetate, gosereline acetate, leuprolide, finasteride, marimastat, bevacizumab, cetuximab, methotrexate, 5-fluorouracil, purine, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, paditaxel, docetaxel, etoposide, teniposide, amsacrine, topotecan, flavopyridols, and bortezomib, kinase inhibitors, methotrexate, 5-fluorouracil, purine, adenosine analogues, cytosine arabinoside, doxorubicin, daunomycin, epirubicin, idarubicin, mitomycin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, paclitaxel, docetaxel, epothilone analogs, discodermolide analogs, eleutherobin analogs, etoposide, teniposide, amsacrine, topotecan, flavopyridols, proteasome inhibitors including bortezomib and biological response modifiers.

7. A pharmaceutical composition comprising at least one compound of claim 2 and a pharmaceutically acceptable carrier.

8. A pharmaceutical composition comprising at least one compound of claim 2 in combination with a pharmaceutically acceptable carrier and at least one other anti-cancer or cytotoxic agent which is selected from the group consisting of tamoxifen, toremifen, raloxifene, droloxifene, iodoxifene, megestrol acetate, anastrozole, letrozole, borazole, exemestane, flutamide, nilutamide, bicalutamide, cyproterone acetate, gosereline acetate, leuprolide, finasteride, marimastat, bevacizumab, cetuximab, methotrexate, 5-fluorouracil, purine, cytosine arabinoside, doxorubicin, daunomycin, epirubicin, idarubicin, mitomvcin-C, dactinomycin, mithramycin, cisplatin, carboplatin, nitrogen mustard, melphalan, chlorambucil, busulphan, cyclophosphamide, ifosfamide, nitrosoureas, thiotepa, vincristine, paditaxel, docetaxel, etoposide, teniposide, amsacrine, topotecan, flavopyridols, and bortezomib.

* * * * *